United States Patent
Viamonte, Jr. et al.

(10) Patent No.: US 6,869,623 B2
(45) Date of Patent: Mar. 22, 2005

(54) NON-TOXIC MUCOSAL DISINFECTANT CONTAINING ISOPROPYL ALCOHOL, SESAME OIL, ALOE, AND LEMON OIL

(76) Inventors: Manuel Viamonte, Jr., 1643 Brickell Ave., Apt. 2805, Miami, FL (US) 33129; Laurence M. Shanley, 662 NE. 195th St., Miami, FL (US) 33179

( * ) Notice: Subject to any disclaimer, the term of this patent is extended or adjusted under 35 U.S.C. 154(b) by 0 days.

(21) Appl. No.: 10/623,816

(22) Filed: Jul. 21, 2003

(65) Prior Publication Data

US 2005/0019430 A1 Jan. 27, 2005

(51) Int. Cl.[7] .......................... A61K 35/78; A61F 13/00
(52) U.S. Cl. ..................... 424/736; 424/725; 424/744; 424/776; 424/443
(58) Field of Search ............................... 424/725, 736, 424/744, 776, 434

(56) References Cited

U.S. PATENT DOCUMENTS

| 4,966,892 | A | * | 10/1990 | McAnalley | 514/54 |
| 5,631,001 | A | * | 5/1997 | Harich et al. | 424/58 |
| 5,908,865 | A | * | 6/1999 | Doi et al. | 514/635 |
| 6,290,964 | B1 | * | 9/2001 | Shupe et al. | 424/744 |
| 6,296,882 | B1 | | 10/2001 | Viamonte, Jr. | |
| 6,488,948 | B1 | * | 12/2002 | Danieli | 424/404 |

* cited by examiner

*Primary Examiner*—Christopher R. Tate
(74) *Attorney, Agent, or Firm*—Laurence A. Greenberg; Werner H. Stemer; Ralph E. Locher

(57) ABSTRACT

A non-toxic mucosal disinfectant for topical application in the nose has a composition of 91% isopropyl alcohol of at least 50% by weight; sesame oil not exceeding 45% by weight, lemon oil of about 2% by weight, aloe of about 5–10% by weight, and optional components of chlorhexidine gluconate and grapefruit seed extract. All of the components are mixed homogeneously, with the sesame oil supplementing and neutralizing the dehydrating effect of the alcohol.

17 Claims, No Drawings

NON-TOXIC MUCOSAL DISINFECTANT CONTAINING ISOPROPYL ALCOHOL, SESAME OIL, ALOE, AND LEMON OIL

BACKGROUND OF THE INVENTION

Field of the Invention

The present invention lies in the pharmacological field of topical disinfectants. More specifically, the invention pertains to a non-toxic mucosal disinfectant that is effective against various pathogenic organisms which cause infectious processes.

The following specification is, to a large extent, related to a commonly assigned U.S. Pat. No. 6,296,882 B1 issued to Manuel Viamonte, Jr. The earlier patent is herewith incorporated by reference in its entirety.

Infectious diseases remain the leading cause of death. While some microorganisms are path ogens (a microorganism capable of causing disease), most microorganisms that are found in the human body are innocuous. For example, more than 600 species of bacteria inhabit the large bowel of a human. Not only are the majority of human microorganisms innocuous but they play useful, if unseen roles. These microorganisms provide a necessary part of the development pathways required for the maturation of human intestinal mucosa and our innate local immune system protects us against harmful microorganisms and helps the digestion of food.

Most of human microbes are commensal. Commensal or transient microbes can be an opportunistic pathogen of humans; namely, they can cause disease if one or more defense mechanisms are breached by accident, medical intent, or an underlying metabolic or even infectious disorder.

Human beings are exposed to nosocomial as well as nosohusial infections. Many microorganisms are adapted exclusively to humans and other animals and many pathogenic microorganisms have learned to circumvent, exploit, subvert or avoid our normal cellular mechanisms to multiply at human expense. Some microbes have made the transition from harmless commensal to potentially fatal infectious agents.

Increases in the world population, rapid travel between distant regions, high concentration of individuals in small areas, the wide spread use of air conditioning and heating equipment without air exchange, the large number of people traveling in confined areas (i.e., aircraft, trains, buses, and automobiles), have resulted in the increase in the number of pathogenic organisms and the increase of mutations of organisms. These effects are currently vividly illustrated by the evolving virus-transmitted SARS pandemic (severe acute respiratory syndrome). Human transfer infections are on the rise in light of the increasing internationalization and the increasing population densities around the world.

Thus, there is a need for effective protective measures to decrease the number and severity of respiratory infections. Some societies use face masks as a protection against respiratory infections—see, for example, the apparent efforts by some Asian and North American populations to protect against SARS infection. In many situations, however, the use of face masks are an impractical, inefficient and largely ineffective way to prevent dissemination of infection.

It is highly desirable to protect the nasal mucosa from pathogenic organisms. In those individuals with active respiratory infection, it is also desirable to decrease the likelihood of dissemination of infection by decreasing the number and/or virulence of the pathogenic organisms expelled during exhaling, sneezing, and/or coughing through the use of a topically applied nasal disinfectant and to also reduce or eliminate disease transmissions through the fingers and hand of an infected person.

SUMMARY OF THE INVENTION

The present invention relates to a non-oxic mucosal disinfectant topically applied which effectively destroys various pathogenic organisms and which does not quickly evaporate and does not substantially interfere with sensory identification of odors.

The present invention further develops the composition disclosed in the above-mentioned U.S. Pat. No. 6,296,882. That nasal antiseptic proved to be very effective as an antiseptic that killed germs in the nose for about 4–6 hours. Alcohol was the main ingredient. While the solution was effective, we continued with our research to further develop and improve the product. The objects presented for improvement included the following:

Pharmaceutical developers and manufacturers demand a solution that is effective for at least 8 hours.

The solution should have a better viscosity for ease of application.

It is imperative that the alcohol-type odor be more completely masked and, further, that the nasal mucosa be better protected against the alcohol.

The antiseptic efficacy with regard to a variety of virus, bacteria, mold, and fungus cannot possibly be high enough, and the potency of the solution should be further increased without increasing the amount of alcohol or other chemicals.

There is an overriding requirement that the solution be stabilized.

With the foregoing and other objects in view there is provided, in accordance with the invention, a non-toxic mucosal disinfectant composition of homogeneously mixed components for topical application in the nose, comprising:

an isopropyl alcohol component of at least 50% by weight;

a sesame oil component not exceeding 45% by weight;

a lemon oil or lemon balm component not exceeding 3% by weight, for supplementing and neutralizing a dehydrating effect of the alcohol; and an aloe or aloe derivative component not exceeding 10% by weight.

In accordance with an added feature of the invention, the aloe component is aloin with emodin.

In accordance with an additional feature of the invention, the sesame oil component is approximately 41% by weight, the lemon oil or lemon balm component is approximately 2% by weight, and the aloe or aloe derivative component is approximately 5% by weight.

In accordance with another feature of the invention, approximately 0.5 to 2% by weight grapefruit seed extract is added, as well as approximately 0.5 to 2% by weight chlorhexidine gluconate.

In accordance with a further feature of the invention, the isopropyl alcohol is at least 91% pure isopropyl alcohol.

With the above and other objects in view there is also provided, in accordance with the invention, a disinfectant composition for treatment of an infection for topical application in the human nose, comprising:

an isopropyl alcohol component of at least 50% by weight;

a sesame oil component not exceeding 45% by weight;

a lemon oil or lemon balm component not exceeding 3% by weight, for supplementing and neutralizing a dehydrating effect of the alcohol; and an aloe or aloe derivative component not exceeding 10% by weight.

In accordance with a preferred embodiment of the invention, the disinfectant composition has the following formula, in % by weight:

50% isopropyl alcohol
2% lemon oil
5% pure aloe gel 5–10% ok
2% chlorhexidine gluconate
41% sesame oil.

In an alternative formulation, the disinfectant composition has, in % by weight:

50% isopropyl alcohol (70–99%)
41% sesame oil
5% aloin
2% lemon oil or lemon balm
0.1% grapefruit seed extract
1% chlorhexidine gluconate.

In accordance with again an added feature of the invention, the isopropyl alcohol component ranges from about 50 to 75% by weight, and the sesame oil component ranges from about 24.9% to 45% by weight.

In accordance with a concomitant feature of the invention, disinfectant composition has an effective treatment life of at least eight hours and a shelf life of at least two years.

In other words, the non-toxic topical disinfectant comprises a novel composition of isopropyl alcohol, sesame oil and lemon oil, in specific relative proportions by weight. The non-toxic topical solution may be used safely to disinfect the nasal mucosa through application of spray or droplets. The invention is a development of the invention described in U.S. Pat. No. 6,296,882. Specifically, we have found that aloe and aloe derivatives are highly effective in the context. In a preferred composition, therefore, we add up to approximately 10% aloe gel.

The underlying object of this invention is to prophylactically apply a solution of the composition comprising isopropyl alcohol, sesame oil, and lemon oil to the distal nasal mucosa (close to the nares) to destroy pathogenic bacteria, viruses and fungi which are present therein and which are inhaled. Normally, present flora is destroyed as well, but repopulates the nose, generally 8 or more hours after the use of the topical disinfectant.

Other features which are considered as characteristic for the invention are set forth in the appended claims.

Although the invention is illustrated and described herein as embodied in a non-toxic mucosal disinfectant, it is nevertheless not intended to be limited to the exemplary details, since various modifications and structural changes may be made therein without departing from the spirit of the invention and within the scope and range of equivalents of the claims.

The novel composition and application, however, together with additional objects and advantages thereof will be best understood from the following description of specific embodiments and examples.

DESCRIPTION OF THE PREFERRED EMBODIMENTS

Numerous disinfectants and delivery systems have been developed aimed at destroying various pathogenic organisms. The chemical and biological effectiveness of such disinfectants are limited by their chemical and biological effects.

The invention of this non-toxic disinfectant composition, by virtue of its most active ingredient (isopropyl alcohol) is effective against various pathogenic organisms which include bacteria (salmonella, staph, pseudomonas, etc.) viruses, (including herpes, and HIV), and fungi, by topical application of this product in the nasal mucosa. The preferred embodiment of the composition comprises 91% isopropyl alcohol 50% by weight, sesame oil 49.5% by weight and lemon oil 0.5% by weight. Other testing has shown effective treatment with isopropyl alcohol being used in a range of about 50 to 75% weight; sesame oil in the range of about 49.5%+ to 24.5%+ and lemon oil in a range of about 0.1 to 0.5%.

The isopropyl alcohol provides the primary bactericidal and virucidal effect (the killing effect of pathogenic organisms) while sesame oil provides lubrication of the nasal mucos or infection area while also acting as a disinfectant. The dehydrating effect of isopropyl alcohol is also neutralized by its dilution with the sesame oil. The lemon oil which is added to the composition provides lubrication, fragrance and vitamin C to the nasal mucosa. Both the sesame oil and lemon oil provide prolonged contact time of the alcohol to the nasal mucosa or infection area (in excess of four hours up to six hours).

The non-toxic mucosal disinfectant of the novel composition includes four distinct components which actively complement each other. One is the primarily active disinfectant, isopropyl alcohol. The others, an additional disinfectant, sesame oil, mixed together with lemon oil, provide mucosal protection which delay the evaporation of the alcohol. The lemon oil adds Vitamin C to the infection site which is effective against infections. The aloe component provides for additional healing properties which are widely known.

Sesame Oil, Ben (n) e, Gingelly, Simsin, til or ufuta Oil is the oil extracted from the seeds of Sesamum indicum (Pedalialceae). Sesame Oil is an oily product which has 22% total fat, 10% of saturated fat, and polyunsaturated and monounsaturated fat. It has no sodium and no carbohydrate as well as no protein and is not a significant source of cholesterol, dietary fiber, vitamin A and C, calcium and iron. The best sesame oil is the 100% pure expeller pressed.

Lemon Oil is an essential oil containing the essence of lemons. It takes 1000 pounds of fresh lemons to make 10 pounds of pure lemon oil. This oil is derived primarily from lemon peels and contains no scents or preservatives. The lemon oil used in the present composition should be 100% pure USP Grade.

Aloe gel (here preferably aloin with emodin) may be present within a wide range. We found that, by way of example, aloe may completely or at least partly replace the chlorhexidine gluconate. In that case, the aloe would be present at about 10%. Aloe is effective for lubrication as well as a component to increase the efficacy of the solution. Additional information with regard to aloe is available, by way of example, at http://www.healthbiz.net.

An initial solution had the following formula:

50% isopropyl alcohol
49.5% sesame oil
0.5% lemon oil.

The initial solution proved effective for up to 6 hours. When another ingredient, chlorhexidine gluconate, was added at 2% by weight, the duration of efficacy was improved to more than 8 hours.

Next, ingredients such as 1 ml/5 ml petroleum jelly (Vaseline®) and 5% tea tree oil were considered. These compositions proved unsuitable and they were rejected. Aloe was then proposed at 5% by weight and it was added instead of a portion of the sesame oil, which was reduced to 43%. Lemon oil was increased to 2% by weight. These considerations led to the following formula:

50% isopropyl alcohol

43% sesame oil

5% aloe gel

2% lemon oil.

Lemon oil was primarily increased for its pleasant fragrance and aloe was added primarily for its lubrication and efficacy.

Grapefruit seed extract (GSE) has more recently been considered as a viable addition. Various studies show that the efficacy of GSE is high even when it is diluted 1:500 or in 0.5–1% solution. Grapefruit seed extract has activated and destroyed bacterial spores at 60 pmm and bacillus subtilis a 2 ppm, which is a cousin of Anthrax. GSE is effective for over 800 bacteria and virus strains, 100 fungus strains, and a great many parasites. It is GRAS approved and it is non-toxic when diluted to 1% or less GRAS, generally recognized/regarded as safe, Groupe de Recherche et d'Action pour la Santé). Finally, GSE has been found to increase shelf life for products and act as a preservative. Information concerning grapefruit seed extract is available, for example, at http://www.pureliquidgold.com/benefits.htm.

EXAMPLE 1

A component of 5% sesame oil was replaced with 5% petroleum jelly (Vaseline®) to create more lubrication and suspension. Example 1 turned out to be a failure. Furthermore, we found research stating the danger of utilizing Vaseline in the nostrils due to reported pulmonary problems such as pneumonia and pulmonary granulomas.

EXAMPLE 2

We replaced 2% sesame oil with 2% chlorhexidine gluconate (FDA approved for nasal mucosa) to solution and were successful with 8 hour efficacy.

EXAMPLE 3

We replaced 1.5% sesame oil with 1.5% lemon oil to mask alcohol-type smell and to increase potency. Lemon oil has very high antiseptic properties and has Vitamin C.

EXAMPLE 4

We replaced 2% sesame oil with 2% glycerin to increase potency and mask alcohol smell. It seems as though alcohol was the most active ingredient and aloe and lemon oil mask alcohol the best.

EXAMPLE 5

We replaced 10% sesame oil with 10% pure aloe gel. This substitution proved to increase potency, mask alcohol smell, act as lubricant and tissue regenerator, enhance breathing and add to solution viscosity. Studies show that aloe kills virus in 15 minutes. Also aloe has superior antiseptic properties to fight bacteria, mold and fungi. According to the International Pharmacopoeia, aloe vera must contain aloin which is derived from the sap. The antiviral/bacterial and fungal properties are: Aloe emodin which consists of anthraquinones which have proven to have antiviral activity to viruses from the same group of enveloped virus which cause the common cold. Other enveloped virus are Infuenza A, B and C, Respiratory Syncytial Virus and Corona Virus.

EXAMPLE 6

We evaluated 5% surgilube gel for suspension. It turned out not to maintain the integrity of the alcohol.

EXAMPLE 7

We evaluated 5% tea tree oil and discovered that the solution was much too unpleasant and seemingly toxic for nasal mucosa.

The project that is outlined with the foregoing examples 1–7 lead to our decision to utilize the following formula:

50% isopropyl alcohol

2% lemon oil

5% pure aloe gel 5–10% ok

2% chlorhexidine gluconate

41% sesame oil 3741% ok

A further formulation, which has been tested and found very effective, is defined by the following formula:

50% isopropyl alcohol (70–99%)

41% sesame oil

5% Aloin (with Emodin) (5–10%)

2% lemon oil or lemon balm

1% grapefruit seed extract

1% chlorhexidine gluconate.

The following text refers to a clinical study which was performed with four human subjects. The four subjects (V,K,L,A) received in the right nostril Sample 1, which is the solution described and claimed in U.S. Pat. No. 6,296,882 B1 (internally referred to as Classic Previn). Subjects V and K received Sample 2 in the left nostril, and Subjects L and A received Sample 3 in the left nostril.

Using a sterile cotton swab (Q-tip®), samples were obtained at 8:00 am, 10:00 am, 12:00 pm, 2:00 pm, and at 4:00 pm. Each sample was spread on Blood Agar, Chocolate Agar and MacConkey dishes.

Samples were obtained at 10:00 am (2 hrs) from the bottom of the nostril. Samples at noon (4 hrs), were obtained from the top of the nostril. Samples at 2 pm (6 hrs), were obtained from the lateral aspect of the nostril and samples at 4 pm (8 hrs) were obtained from the medial aspect of the nostril.

Cultured bacteria were counted 24 hours later and photographed with a digital camera. Photographs were made of the baseline blood agar plate of each of the four subjects and then the composite images were obtained at 2,4,6 and 8 hours of blood agar and chocolate agar plates on each of the four subjects.

It is of interest to note that in subject A at 2 hours, a sample was obtained from the left nostril from secretions. Subject K sneezed just before obtaining samples at 8 hours. Subject L mentioned that he touched his nostril a few times after 12 pm.

It was discovered that the novel composition continued throughout the 8 hour period killing germs and baseline germ count had still not returned to normal. It was noted that 3 subjects at one point or another had a germ colony count over 100 and the novel composition (Previn) was able to kill germ colonies to under 30 even after 6 hours. This reinfection could be due to nasal secretion from cold, sneezing, touching the nose with hands or respiratory pathogens.

Colony counts of growth from left nostril and right nostril.

| Pt V | Sample 2 | | | Sample 1 | | |
|---|---|---|---|---|---|---|
| | BAP-L | CHOC-L | MAC-L | BAP-R | CHOC-R | MAC-R |
| Baseline | >100 | >100 | 0 | >100 | >100 | 0 |
| 2 hours | 4 | 2 | 0 | 6 | 15 | 0 |
| 4 hours | 14 | 7 | 0 | 37 | 46 | 0 |
| 6 hours | 18 | 12 | 0 | 25 | 8 | 0 |
| 8 hours | 27 | 16 | 0 | 25 | 8 | 0 |

| Pt L | Sample 3 | | | Sample 1 | | |
|---|---|---|---|---|---|---|
| | BAP-L | CHOC-L | MAC-L | BAP-R | CHOC-R | MAC-R |
| Baseline | 82 | >100 | 3 | 41 | 75 | 0 |
| 2 hours | 4 | 5 | 0 | 25 | 66 | 25 |
| 4 hours | >100 | >100 | 6 | 40 | 40 | 0 |
| 6 hours | 22 | 10 | 0 | 50 | 13 | 0 |
| 8 hours | 88 | 65 | 12 | 65 | 30 | 7 |

| Pt K | Sample 2 | | | Sample 1 | | |
|---|---|---|---|---|---|---|
| | BAP-L | CHOC-L | MAC-L | BAP-R | CHOC-R | MAC-R |
| Baseline | >100 | 69 | 0 | >100 | >100 | 0 |
| 2 hour | 14 | 9 | 0 | 0 | 0 | 0 |
| 4 hour | >100 | 3 | 0 | >100 | 0 | 0 |
| 6 hour | 28 | 14 | 0 | 7 | 3 | 0 |
| 8 hour | 26 | 15 | 0 | 0 | 3 | 0 |

| Pt A | Sample 3 | | | Sample 1 | |
|---|---|---|---|---|---|
| | BAP-L | CHOC-L | MAC-L | BAP-R | CHOC-R |
| Baseline | >100 | 90 | 0 | >100 | >100 | 0 |
| 2 hours | 10 | 9 | 0 | 30 | 55 | 0 |
| 4 hours | 3 | 0 | 0 | 59 | 80 | 0 |
| 6 hours | 88 | 50 | 0 | >100 | 83 | 0 |
| 8 hours | 46 | 15 | 0 | 31 | 34 | — |

BAP = blood agar plate, general all purpose media capable of growing most aerobic and facultative anarobic organisms.
CHOC = chocolate agar (lysed blood) plate, which is an enriched media that allows growth of most organisms on BAP plus some fastidious organisms, such as *Haemophilus*.
MAC = Maconkey agar, which is an inhibitory selective media for gram negative organisms, all respiratory flora will not grow on this media.

Comparison of all patients for Sample 1 (right nostril) for growth on Chocolate agar plate (CHOC).

| Time | Pt V | Pt K | Pt L | Pt A |
|---|---|---|---|---|
| Baseline | >100 | >100 | 75 | >100 |
| 2 hour | 15 | 0 | 66 | 55 |
| 4 hour | 46 | 0 | 40 | 80 |
| 6 hour | 8 | 3 | 13 | 83 |
| 8 hour | 8 | 3 | 30 | 34 |

>100 = indicate more than 100 colonies of growth on the plate.

Comparison of patients for Sample 2 and Sample 3 (left nostril) for growth on CHOC.

| | Sample 2 | | Sample 3 | |
|---|---|---|---|---|
| Time | Pt V | Pt K | Pt L | Pt A |
| Baseline | >100 | 69 | >100 | 90 |
| 2 hours | 2 | 9 | 5 | 9 |
| 4 hours | 7 | 3 | >100 | 0 |
| 6 hours | 12 | 14 | 11 | 50 |
| 8 hours | 16 | 15 | 65 | 15 |

Finally, we tested two patients with respectively different preparations and bacteria growth measured at 2, 4, 6, and 8 hours; Colony counts after 24 hours of growth on blood agar media. One colony is approximately 100,000 bacteria.

| | Patient 1 | | Patient 2 | |
|---|---|---|---|---|
| | Left Nostril | Right Nostril | Left Nostril | Right Nostril |
| Preparation | A | P | G | P |
| Baseline | >200 | >200 | >200 | >200 |
| 2 hours | 0 | 19 | 17 | 7 |
| 4 hours | 0 | 6 | 90 | 46 |
| 6 hours | 55 | 2 | 20 | 14 |
| 8 hours | 63 | 17 | 15 | 0 |

Preparations:
P = original preparation (U.S. Pat. No. 6,296,882 B1).
A = P + aloe
G = P + aloe + grapefruit seed extract

We claim:

1. A non-toxic mucosal disinfectant composition of homogeneously mixed components for topical application in the nose, comprising:
   an isopropyl alcohol component of at least 50% by weight;
   a sesame oil component not exceeding 45% by weight;
   a lemon oil or lemon balm component not exceeding 3% by weight, for supplementing and neutralizing a dehydrating effect of said alcohol; and
   an aloe component not exceeding 10% by weight.

2. The disinfectant composition according to claim 1, wherein said aloe component is aloin with emodin.

3. The disinfectant composition according to claim 1, wherein said sesame oil component is approximately 41% by weight, said lemon oil or lemon balm component is approximately 2% by weight, and said aloe component is approximately 5% by weight.

4. The disinfectant composition according to claim 1, which further comprises approximately 0.5 to 2% by weight grapefruit seed extract and approximately 0.5 to 2% by weight chlorhexidine gluconate.

5. The disinfectant composition according to claim 1, wherein said isopropyl alcohol is at least 91% pure isopropyl alcohol.

6. The disinfectant composition according to claim 1, which comprises the following formula, in % by weight:
   50% isopropyl alcohol
   2% lemon oil
   5% pure aloe gel 5–10% ok
   2% chlorhexidine gluconate
   41% sesame oil.

7. The disinfectant composition according to claim 1, which comprises the following formula, in % by weight:
   50% isopropyl alcohol (70–99%)
   41% sesame oil 5% aloin 2% lemon oil or lemon balm 1% grapefruit seed extract 1% chlorhexidine gluconate.

8. The disinfectant composition according to claim 1, wherein said isopropyl alcohol component ranges from about 50 to 75% by weight, and said sesame oil component ranges from about 24.9% to 45% by weight.

9. The disinfectant composition according to claim 1, wherein the composition has an effective treatment life of at least eight hours and a shelf life of at least two years.

10. A disinfectant composition for treatment of an infection for topical application in the human nose, comprising:

an isopropyl alcohol component of at least 50% by weight;

a sesame oil component not exceeding 45% by weight;

a lemon oil or lemon balm component not exceeding 3% by weight, for supplementing and neutralizing a dehydrating effect of said alcohol; and an aloe component not exceeding 10% by weight.

11. The disinfectant composition according to claim 10, wherein said aloe component is aloin with emodin.

12. The disinfectant composition according to claim 10, wherein said sesame oil component is approximately 41% by weight, said lemon oil or lemon balm component is approximately 2% by weight, and said aloe component is approximately 5% by weight.

13. The disinfectant composition according to claim 10, which further comprises approximately 0.5 to 2% by weight grapefruit seed extract and approximately 0.5 to 2% by weight chlorhexidine gluconate.

14. The disinfectant composition according to claim 10, wherein said isopropyl alcohol is at least 91% pure isopropyl alcohol.

15. The disinfectant composition according to claim 10, wherein the composition has an effective treatment life of at least eight hours.

16. The disinfectant composition according to claim 10, which comprises the following formula, in % by weight:

50% isopropyl alcohol

2% lemon oil

5% pure aloe gel 5–10%

2% chlorhexidine gluconate

41% sesame oil.

17. The disinfectant composition according to claim 10, which comprises the following formula, in % by weight:

50% isopropyl alcohol (70–99%)

41% sesame oil

5% aloin

2% lemon oil or lemon balm

1% grapefruit seed extract

1% chlorhexidine gluconate.

* * * * *